US012642991B2

(12) United States Patent
Stanchev et al.

(10) Patent No.: US 12,642,991 B2
(45) Date of Patent: Jun. 2, 2026

(54) SETUP FOR TREATMENT PLANNING SCANS IN A RADIATION THERAPY SYSTEM

(71) Applicant: SIEMENS HEALTHINEERS INTERNATIONAL AG, Steinhausen (CH)

(72) Inventors: Sevelin Stanchev, Las Vegas, NV (US); Stephen Thompson, Pacific Grove, CA (US)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 412 days.

(21) Appl. No.: 17/881,592

(22) Filed: Aug. 4, 2022

(65) Prior Publication Data

US 2024/0042240 A1    Feb. 8, 2024

(51) Int. Cl.
*A61N 5/10*              (2006.01)

(52) U.S. Cl.
CPC ......... *A61N 5/1049* (2013.01); *A61N 5/1081* (2013.01); *A61N 2005/1061* (2013.01); *A61N 2005/1074* (2013.01)

(58) Field of Classification Search
CPC .... A61N 2005/1074; A61N 2005/1061; A61N 5/103; A61B 6/03
See application file for complete search history.

(56) References Cited

U.S. PATENT DOCUMENTS

| | | | | |
|---|---|---|---|---|
| 7,502,445 B2 * | 3/2009 | Shi | ......................... | A61B 6/032 378/115 |
| 11,110,300 B2 * | 9/2021 | Van Heteren | ........ | A61N 5/1081 |
| 12,053,650 B2 * | 8/2024 | Vojan | ..................... | A61N 5/103 |

(Continued)

OTHER PUBLICATIONS

Non-Published Commonly Owned U.S. Patent Application, Filed on Aug. 4, 2022 , 35 pages.

*Primary Examiner* — David J Makiya
*Assistant Examiner* — Miya Downing
(74) *Attorney, Agent, or Firm* — SU IP CONSULTING

(57) ABSTRACT

A method for a radiation treatment system includes: a treatment-delivering X-ray source configured to rotate about an isocenter of the radiation treatment system and direct treatment X-rays to a target volume; an imaging X-ray source configured to rotate about the isocenter of the radiation treatment system and direct imaging X-rays to a target region that includes the target volume; and a processor. The processor is configured to perform the steps of: displaying a first set of multiple first user input elements, wherein each first user input element corresponds to a different anatomical region; in response to receiving a first user input via a specific first user input element included in the first set, displaying a second set of multiple second user input elements, wherein each second user input element corresponds to a different imaging protocol for an anatomical region that is associated with the specific first user input element in the first set; and in response to receiving a second user input via a specific second user input element included in the second set, acquiring at least one X-ray image of the target region via the imaging X-ray source and an imaging protocol that is associated with the specific second user input element.

20 Claims, 15 Drawing Sheets

(56)                    References Cited

U.S. PATENT DOCUMENTS

| | | | |
|---|---|---|---|
| 2014/0098932 A1* | 4/2014 | Profio | G16H 40/63 |
| | | | 378/19 |
| 2015/0297166 A1 | 10/2015 | Goto et al. | |
| 2016/0174930 A1 | 6/2016 | Braun et al. | |
| 2017/0143291 A1 | 5/2017 | Guntzer et al. | |
| 2020/0030634 A1 | 1/2020 | Van Heteren et al. | |
| 2021/0244376 A1 | 8/2021 | Buelow et al. | |
| 2022/0061781 A1 | 3/2022 | Zhao | |
| 2022/0203134 A1 | 6/2022 | Givehchi et al. | |
| 2023/0154594 A1* | 5/2023 | Choudhury | G16H 30/40 |

\* cited by examiner

100

101    102    102    101

103

107

106

105

REMOTE CONTROL
CONSOLE
110

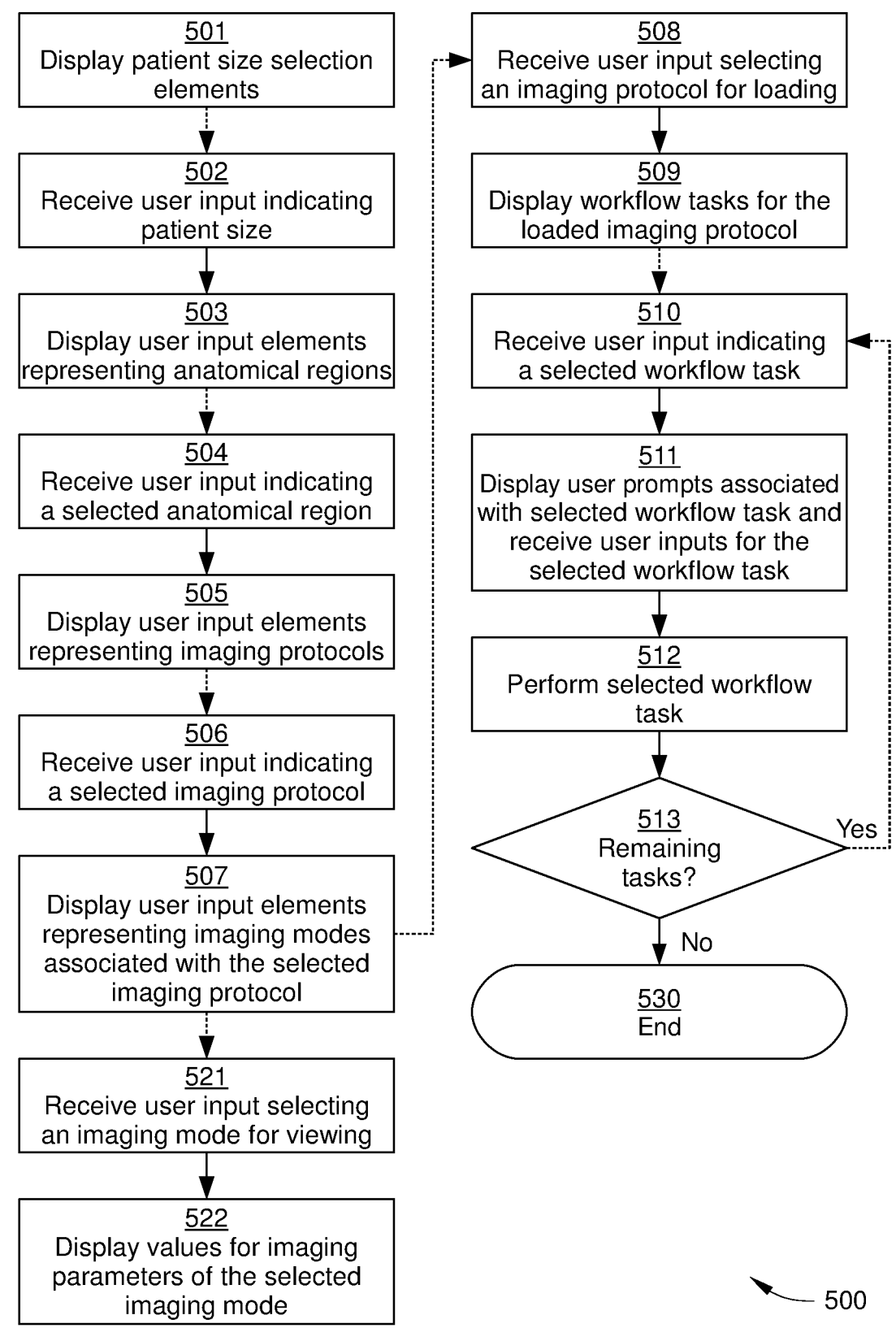

501
Display patient size selection elements

502
Receive user input indicating patient size

503
Display user input elements representing anatomical regions

504
Receive user input indicating a selected anatomical region

505
Display user input elements representing imaging protocols

506
Receive user input indicating a selected imaging protocol

507
Display user input elements representing imaging modes associated with the selected imaging protocol

521
Receive user input selecting an imaging mode for viewing

522
Display values for imaging parameters of the selected imaging mode

508
Receive user input selecting an imaging protocol for loading

509
Display workflow tasks for the loaded imaging protocol

510
Receive user input indicating a selected workflow task

511
Display user prompts associated with selected workflow task and receive user inputs for the selected workflow task

512
Perform selected workflow task

513
Remaining tasks?

Yes

No

530
End

SETUP FOR TREATMENT PLANNING SCANS IN A RADIATION THERAPY SYSTEM

CROSS REFERENCE TO RELATED APPLICATION

The present application is related in subject matter to U.S. patent application Ser. No. 17/881,593, which issued as U.S. Pat. No. 12,582,368 B2.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. For example, a treatment planning scan is often performed via computed tomography (CT) to generate the three-dimensional image. From such imaging, the size and mass of the target tissue can be estimated, a planning target volume determined, and an appropriate treatment plan generated.

So that the prescribed dose is correctly supplied to the planning target volume during radiation therapy, a patient must be correctly positioned relative to the linear accelerator that provides the radiation therapy. Typically, the patient must be precisely positioned so that the planning target volume is located at the isocenter about which the linear accelerator rotates. To that end, the location of the planning target volume is pinpointed when the treatment planning images are generated, and external patient markings are made that indicate the location of the planning target volume at the time of treatment. For example, based on the location of the planning treatment volume determined via treatment planning images, a laser-based system can indicate precise locations on the patient for external markings that have a specified relationship to the planning treatment volume. Such external patient markings enable the correct positioning of the patient, and therefore the planning target volume, with respect to a linear accelerator isocenter at the time of treatment.

Historically, for image-guided radiotherapy, a treatment planning scan is acquired with a dedicated treatment planning imager (such as a standalone CT imaging system), while the treatment plan that is based on the treatment planning scan is delivered with a radiation therapy system that has an onboard imaging system. Because the treatment planning imaging system and the radiation therapy system have different coordinate systems, treatment errors can occur. For example, according to analysis of the Radiation Oncology Incident Learning System (RO-ILS), two of the three major error pathways leading to an incorrect radiation treatment are "wrong shift instructions" and "wrong shift performed at treatment."

"Wrong shift instruction" errors can occur when the location of a planning target volume is incorrectly converted from the coordinate system of a treatment planning imager to the coordinate system of an associated laser-marking system, resulting in erroneous locations for external patient markings. Frequently, incorrect conversions occur due to human error in the various steps of the patient-marking process, such as calculating the shift needed to position the planning treatment volume in a particular position for laser marking, manually entering location information from one coordinate system into another system, positioning one or more lasers of the laser-marking system, etc. "Wrong shift performed at treatment" errors can occur when a tumor or other planning target volume that is imaged on a dedicated treatment planning imager is located with a large offset from the center of the treatment planning images. For example, a physical shift of the radiation treatment system couch that is needed to compensate for such an offset exceeds the range of motion of the radiation treatment system couch and/or results in a collision with a portion of the radiation treatment system.

As the quality of onboard imaging systems improves, it is possible for treatment planning scans can now be acquired with the same radiation therapy system that subsequently delivers the treatment plan, rather than with a separate CT imaging system. Consequently, errors resulting from the treatment planning imaging system and the radiation therapy system having different coordinate systems for patient positioning can be avoided, such as "wrong shift instructions" and "wrong shift performed at treatment."

One drawback to acquiring a treatment planning scan with the same radiation treatment system that delivers the treatment plan is that such an approach places additional demands on the radiation therapist or other user of the radiation therapy system. In particular, the radiation therapist or other user must be conversant in both the implementation of treatment protocols on the radiation therapy system and the setup of the radiation therapy system for treatment planning scans. For a particular patient, treatment planning scans can be implemented using a wide variety of imaging parameters that affect planning image quality and patient dosing, including scanning start and end locations, gantry tilt, field of view, scanning energy and tube current, exposure time, the number of projection images, and the like. In addition, unlike the delivery of a treatment plan, there is generally very little guidance for the user in how a particular treatment planning scan session should be performed. For instance, the user may be given no more information than which anatomical region on which to perform the treatment planning scan and perhaps a specific immobilizer to employ. However, for a particular anatomical region, an imaging system typically has a large number of different predetermined imaging modes that can be selected, each having a different dosing, image quality, optimal application (e.g., patient size and patient orientation), and the like. In light of the above, setting up the onboard imaging system of a radiation therapy system for a treatment planning scan can be time-consuming and difficult to optimize. As a result, specific training is required to enable a user to efficiently navigate the many imaging modes and parameters associated with treatment planning scans and to acquire treatment planning scans with an onboard imaging system of a radiation therapy system.

Accordingly, there is a need in the art for techniques to facilitate the setup of a radiation therapy system for a treatment planning scan.

SUMMARY

In accordance with at least some embodiments, a user interface of a radiation therapy system provides a structured workflow that enables a user of the radiation therapy system to efficiently setup and perform a treatment planning scan. The structured workflow guides the user in a repeatable, easily followed process that ensures selection of the optimal imaging modes for a particular treatment planning scan session. Further, in some embodiments, the user interface enables the user to review the specific imaging modes and associated imaging parameter settings prior to being selected, which enables the user to confirm that the appropriate imaging mode is selected before being performed.

In accordance with at least some embodiments, a radiation therapy system includes: a treatment-delivering X-ray source configured to rotate about an isocenter of the radiation treatment system and direct treatment X-rays to a target volume; an imaging X-ray source configured to rotate about the isocenter of the radiation treatment system and direct imaging X-rays to a target region that includes the target volume; and a processor. The processor is configured to perform the steps of: displaying a first set of multiple first user input elements, wherein each first user input element corresponds to a different anatomical region; in response to receiving a first user input via a specific first user input element included in the first set, displaying a second set of multiple second user input elements, wherein each second user input element corresponds to a different imaging protocol for an anatomical region that is associated with the specific first user input element in the first set; and in response to receiving a second user input via a specific second user input element included in the second set, acquiring at least one X-ray image of the target region via the imaging X-ray source and an imaging protocol that is associated with the specific second user input element.

In accordance with at least some embodiments, a method for a radiation therapy system that includes a treatment-delivering X-ray source configured to rotate about an isocenter of the radiation treatment system and an imaging X-ray source configured to rotate about the isocenter of the radiation treatment system includes: displaying a first set of multiple first user input elements, wherein each first user input element corresponds to a different anatomical region; in response to receiving a first user input via a specific first user input element included in the first set, displaying a second set of multiple second user input elements, wherein each second user input element corresponds to a different imaging protocol for an anatomical region that is associated with the specific first user input element in the first set; and in response to receiving a second user input via a specific second user input element included in the second set, acquiring at least one X-ray image of the target region by rotating the imaging X-ray source about the isocenter based on an imaging protocol that is associated with the specific second user input element.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

FIG. 5 sets forth a flowchart of a method for the setup and performance of treatment planning scans in a radiation therapy system, according to one or more embodiments.

DETAILED DESCRIPTION

Figure 1:
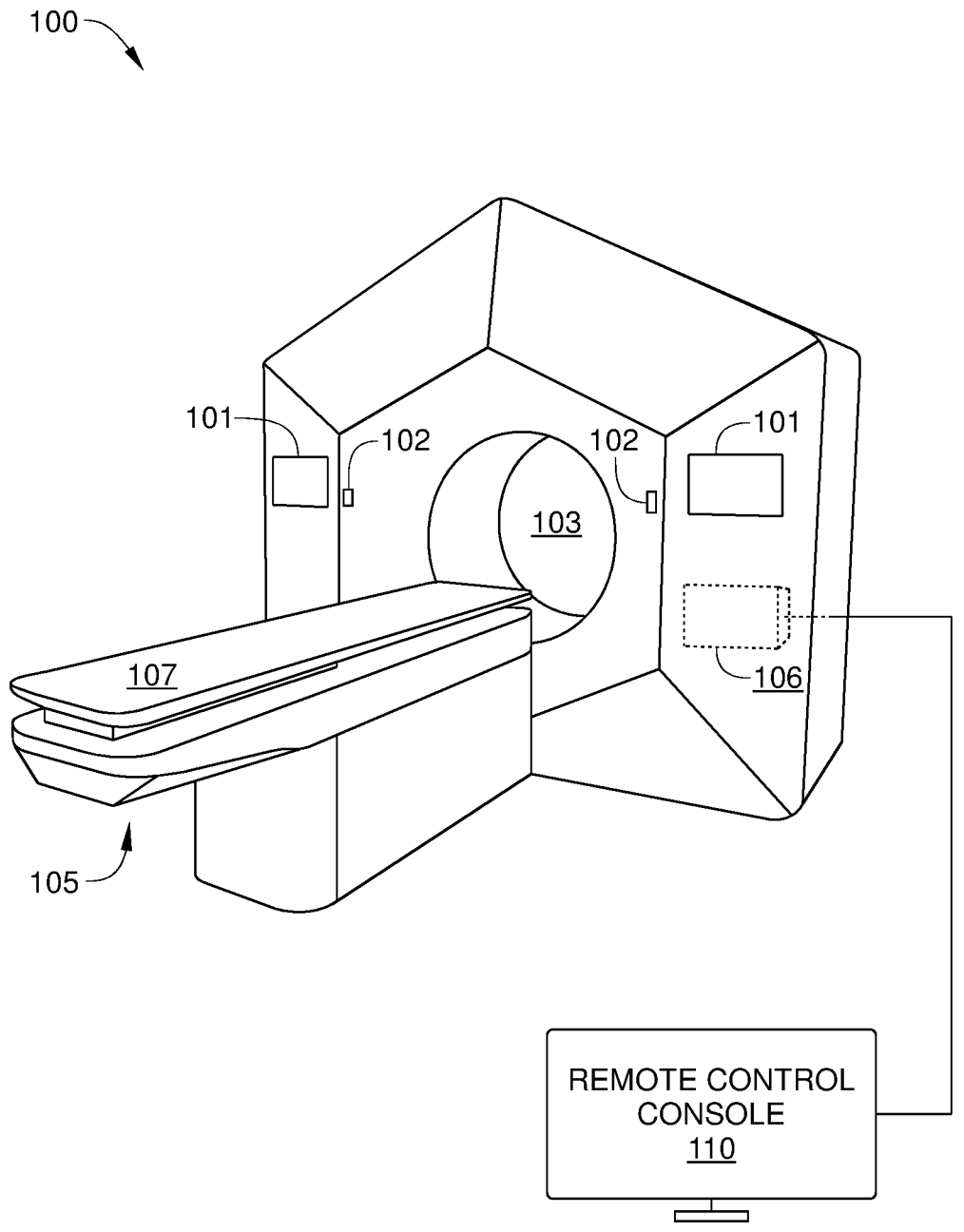
FIG. 1 is a perspective view of a radiation therapy system, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a perspective view of a radiation therapy (RT) system 100, according to various embodiments. RT system 100 is configured to image patient anatomy surrounding a planning target volume, such as a tumor, and reconstruct a digital volume of the patient anatomy that includes the planning target volume. In some embodiments, radiation therapy system 100 performs such imaging via a cone-beam computed tomography (CBCT) process using one or more imagers incorporated in radiation therapy system 100, such as one or more kilovolt (kV) X-ray imagers. In some embodiments, RT system 100 is a radiation system configured to detect inter-fraction motion using X-ray imaging techniques. In some embodiments, RT system 100 is a radiation system configured to detect intra-fraction motion in near-real time using X-ray imaging techniques. Thus, in such embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, RT system 100 is described herein configured with a circular gantry. In other embodiments, RT system 100 can be configured with a C-gantry capable of infinite rotation via a slip ring connection.

Generally, RT system 100 is capable of kV imaging of a target volume, to generate treatment planning image information (such as a treatment planning scan) and/or to generate images during a radiation therapy treatment fraction. Thus, in some embodiments, RT system 100 can be employed in addition to or instead of a treatment planning computed tomography imager. Further, in some embodiments, RT system is configured to image a target volume immediately prior to and/or during application of an MV treatment beam, so that an image-guided radiation therapy (IGRT) process and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
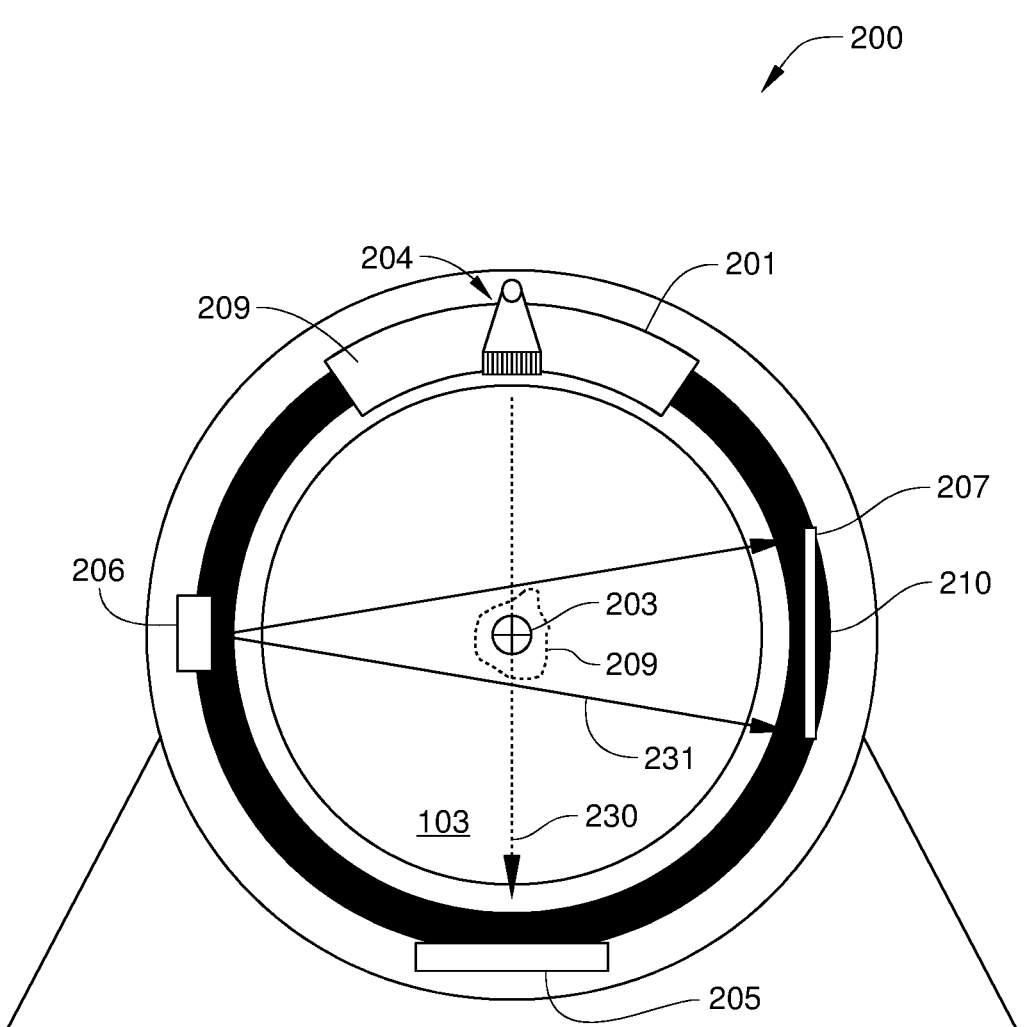
FIG. 2 schematically illustrates a drive stand and gantry of the radiation therapy system of FIG. 2, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT system 100, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT system 100, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. In some embodiments, CBCT can be employed to generate treatment planning images. Additionally or alternatively, in some embodiments, CBCT is employed at the beginning of a radiation therapy session to generate a set-up 3D reconstruction. For example, CBCT may be employed immediately prior to application of treatment beam 230 to generate a 3D reconstruction confirming that: target volume 209 has not moved relative to isocenter 203 or changed shape; target volume 209 is aligned precisely to treatment beam 230; and/or target volume 209 has not significantly changed position relative to organs at risk (e.g., due to bladder, intestine, or rectum filling). Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
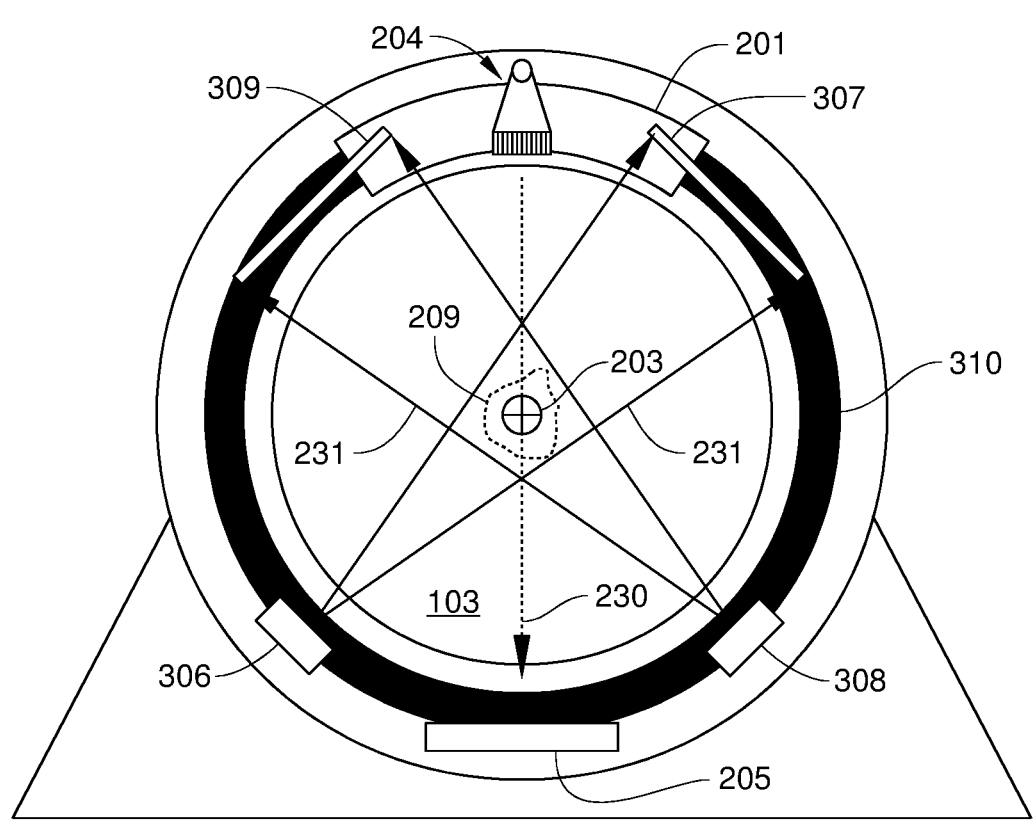
FIG. 3 schematically illustrates a drive stand and a gantry of the radiation therapy system of FIG. 2, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 210 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 4.

Figure 4:
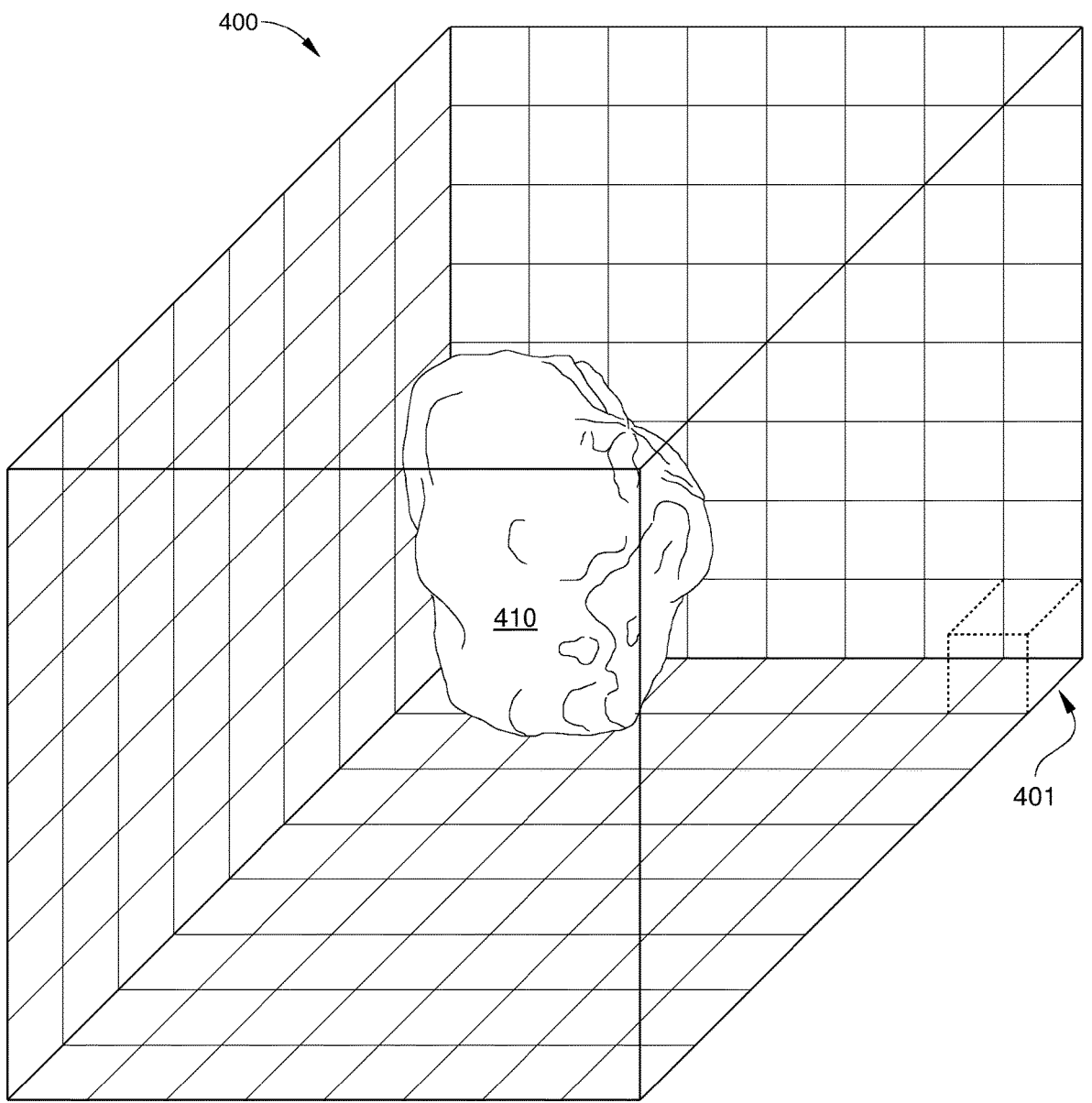
FIG. 4 schematically illustrates a digital volume that is constructed based on projection images of an anatomical region generated by one or more X-ray imagers included in the radiation therapy system of FIG. 2, according to various embodiments.

FIG. 4 schematically illustrates a digital volume 400 that is constructed based on projection images of an anatomical region generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the GTV, CTV, or the PTV for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, according to various embodiments, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to be extending outside a threshold region, the treatment can either be aborted or modified. In such an instance, modification of the treatment can be accomplished by adjusting patient position and/or the treatment beam.

Setup for Treatment Planning Scans

According to various embodiments, a user interface (UI) of a radiation therapy system provides a structured workflow that enables a user of the radiation therapy system to select and implement an appropriate imaging protocol for a particular treatment planning scan. Specifically, the UI-based workflow walks the user through a step-by-step procedure so that an appropriate imaging protocol for a particular treatment planning scan is selected and performed. Thus, from the very large number of available imaging protocols that have been defined for the radiation therapy system and can be employed for a treatment planning scan, the user is guided to the selection of one of the imaging protocols best suited for the particular application.

Each available imaging protocol is associated with a specific patient size (e.g., adult or child) and anatomical region (e.g., head, neck/spine, right thorax, left thorax, right abdomen, left abdomen, right pelvis, left pelvis, upper extremity, lower extremity, etc.). In addition, each available imaging protocol includes one or more session images to be acquired, where each session image generally corresponds to a different imaging mode. For example, the imaging protocol for a particular treatment planning scan may include three session images: a topogram, a CBCT-for-planning image, and a CBCT-for-planning image with a contrast medium. In another example, the imaging protocol for a different treatment planning scan may include a topogram and a CBCT-for-planning image, and no image with a contrast medium.

In some embodiments, each session image is associated with a specific imaging mode. That is, each session image includes a specific, and generally unique, combination of imaging parameter values. Examples of such imaging parameter values include: scanning start location, scanning end location, gantry tilt, field of view, scanning energy (kV), tube current (mAs), exposure time, exposure/dose (mSv), the number of projection images acquired for the session image, patient position, patient orientation, and the like. In some embodiments, each session image further includes values for one or more image reconstruction parameters, such as an indicator of the specific reconstruction algorithm to be employed when generating a digital volume based on the session image or a desired slice thickness.

FIG. 5 sets forth a flowchart of a method 500 for the setup and performance of treatment planning scans in a radiation therapy system, according to one or more embodiments. Method 500 may include one or more operations, functions, or actions as illustrated by one or more of blocks 501-530. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although method 500 is described in conjunction with RT system 100 and FIGS. 1-4, persons skilled in the art will understand that any suitably configured radiation therapy system is within the scope of the present embodiments. FIGS. 6A-6H schematically illustrate a graphical user interface (GUI) 600 of RT system 100 displayed by a remote display screen and/or a treatment room display screen at certain steps of method 500, according to various embodiments.

Method 500 is generally performed in response to a particular patient receiving a diagnosis that necessitates radiation therapy and thus the generation of a radiation therapy treatment plan. As noted previously, such a treatment plan is typically generated based on a digital volume, such as digital volume 400, that includes a target volume, such as target volume 410. According to various embodiments, the digital volume is reconstructed based on imaging information obtained via a treatment planning scan that is performed using onboard imaging of RT system 100 as described below. Prior to the herein-described treatment planning scan, the patient is positioned on couch 107. In some instances, the patient is positioned in conjunction with prescribed immobilization, so that a suitable patient position is maintained during the treatment planning scan. Alternatively or additionally, in some instances, the patient is administered with a prescribed contrast medium, which can be ingested or administered intravenously.

Figure 6A:
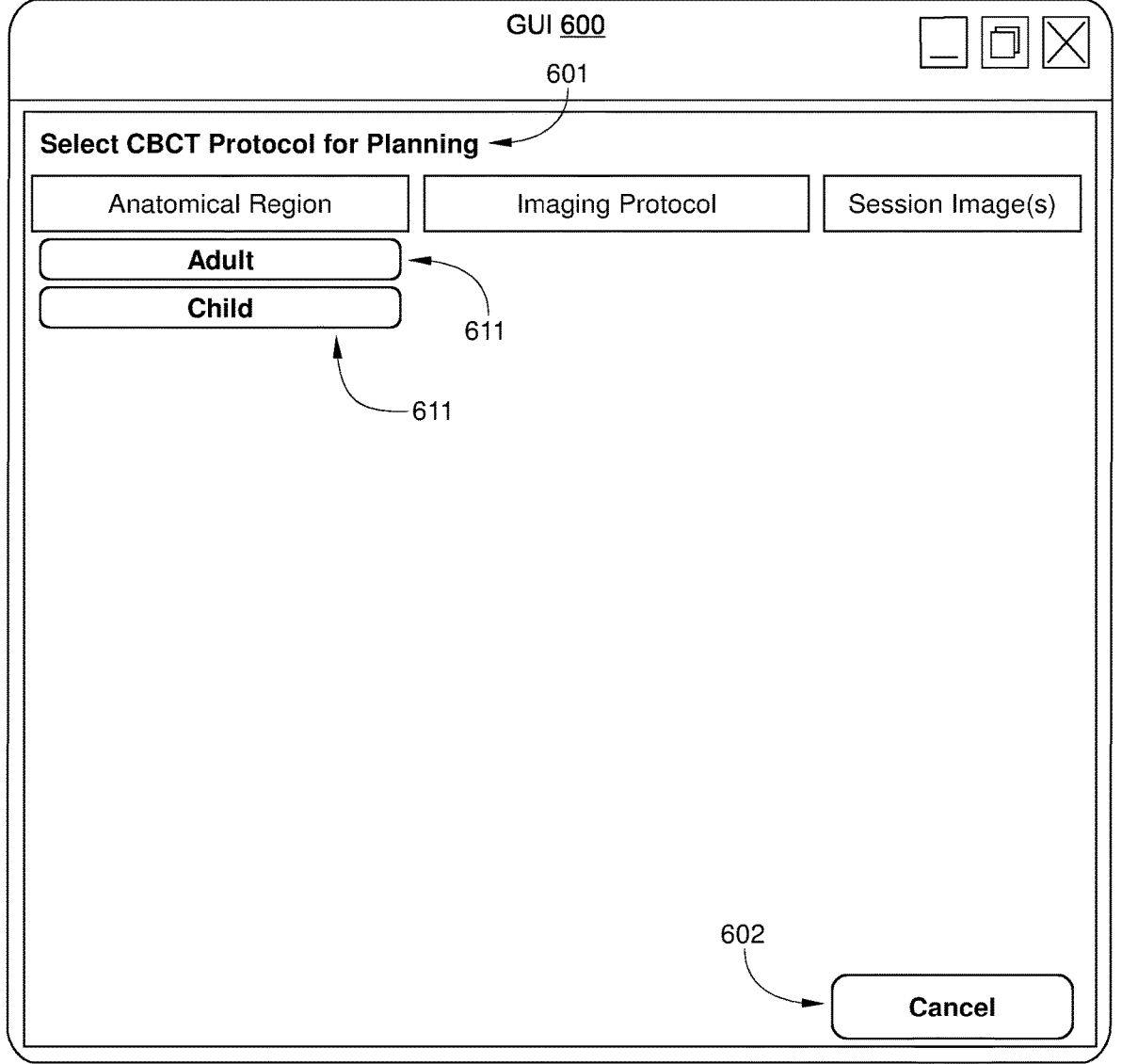
FIGS. 6A, 6B, 6C, 6D, 6E, 6F, 6G and 6H schematically illustrate a graphical user interface of a radiation therapy system displayed by a remote display screen and/or a treatment room display screen at certain steps of the method FIG. 5, according to various embodiments.

Method 500 begin at step 501, where RT system 100 displays a GUI 600 at a display screen, as shown in FIG. 6A. For example, in some embodiments, the display screen is a display screen associated with remote control console 110. Alternatively or additionally, in some embodiments, GUI 600 displays GUI 600 at a treatment room display, such as touchscreen 101. In either case, GUI 600 includes a user prompt 601, multiple patient size selection elements 611, and in some embodiments a cancel button 602 for halting method 500. User prompt 601 provides textual information and/or a visual reminder indicating a required action or step that is to be performed by the user. For example, in the embodiment illustrated in FIG. 6A, user prompt 601 textually indicates that the user must "select a CBCT protocol for planning." Each of the multiple patient size selection elements 611 indicates a particular size category for the current patient. For example, in the embodiment illustrated in FIG. 6A, there are patient size selection elements 611 for two categories of patient size: "Adult" and "Child." In other embodiments, patient size selection elements 611 can include more than two categories of patient size, such as "Large Adult," "Average Adult," "Small Adult," "Large Child," and/or "Small Child," and the like. In such embodiments, imaging protocols that have been established for a higher granularity of different patient sizes can be easily selected by the user based on this organizational scheme.

Figure 6B:
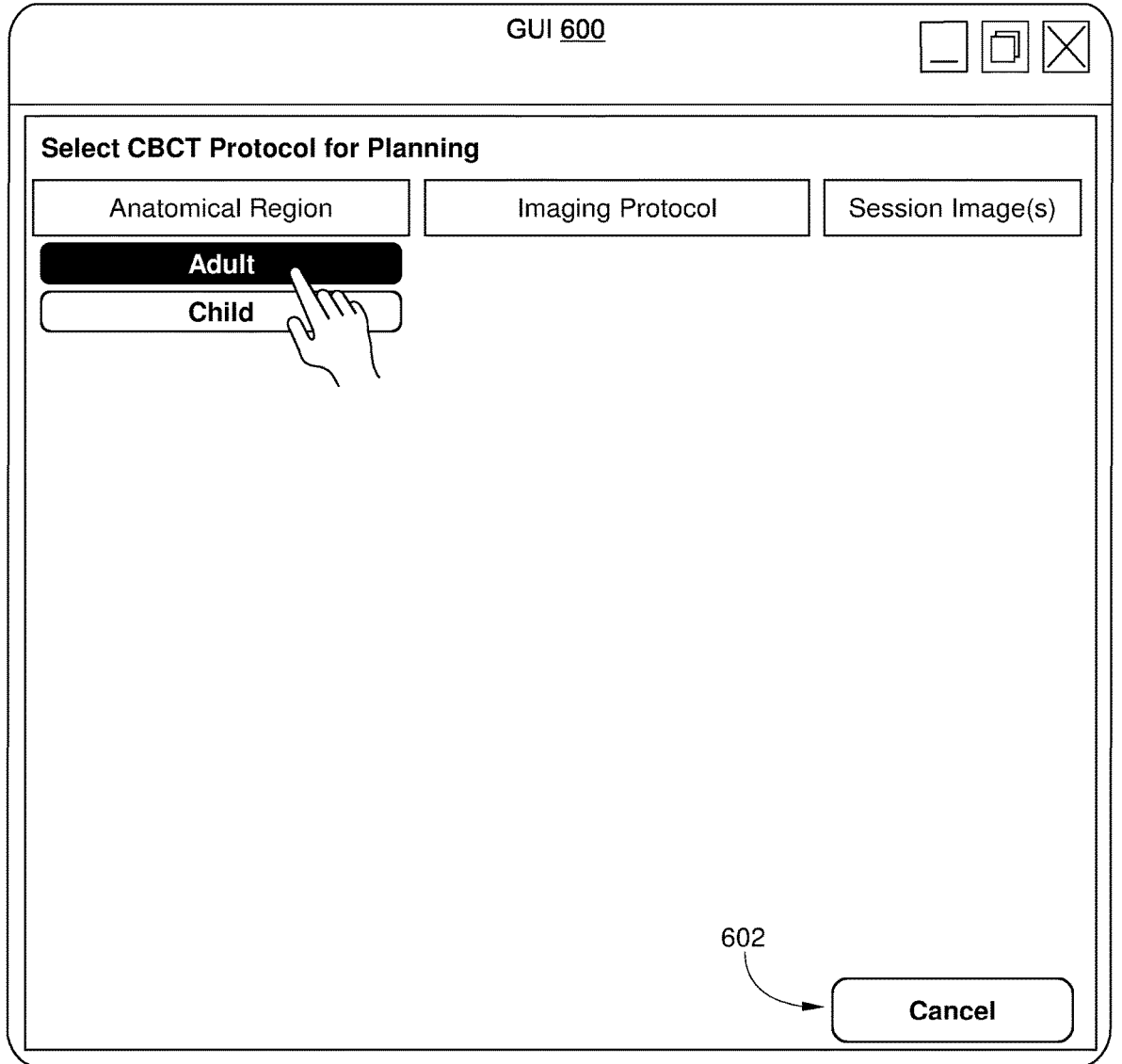

In step 502, RT system 100 receives a user input indicating a particular patient size, for example via GIU 600, as shown in FIG. 6B. In some embodiments, the user input can be received when the user makes an appropriate selection with GUI 600, for example via a mouse click or finger tap.

Figure 6C:
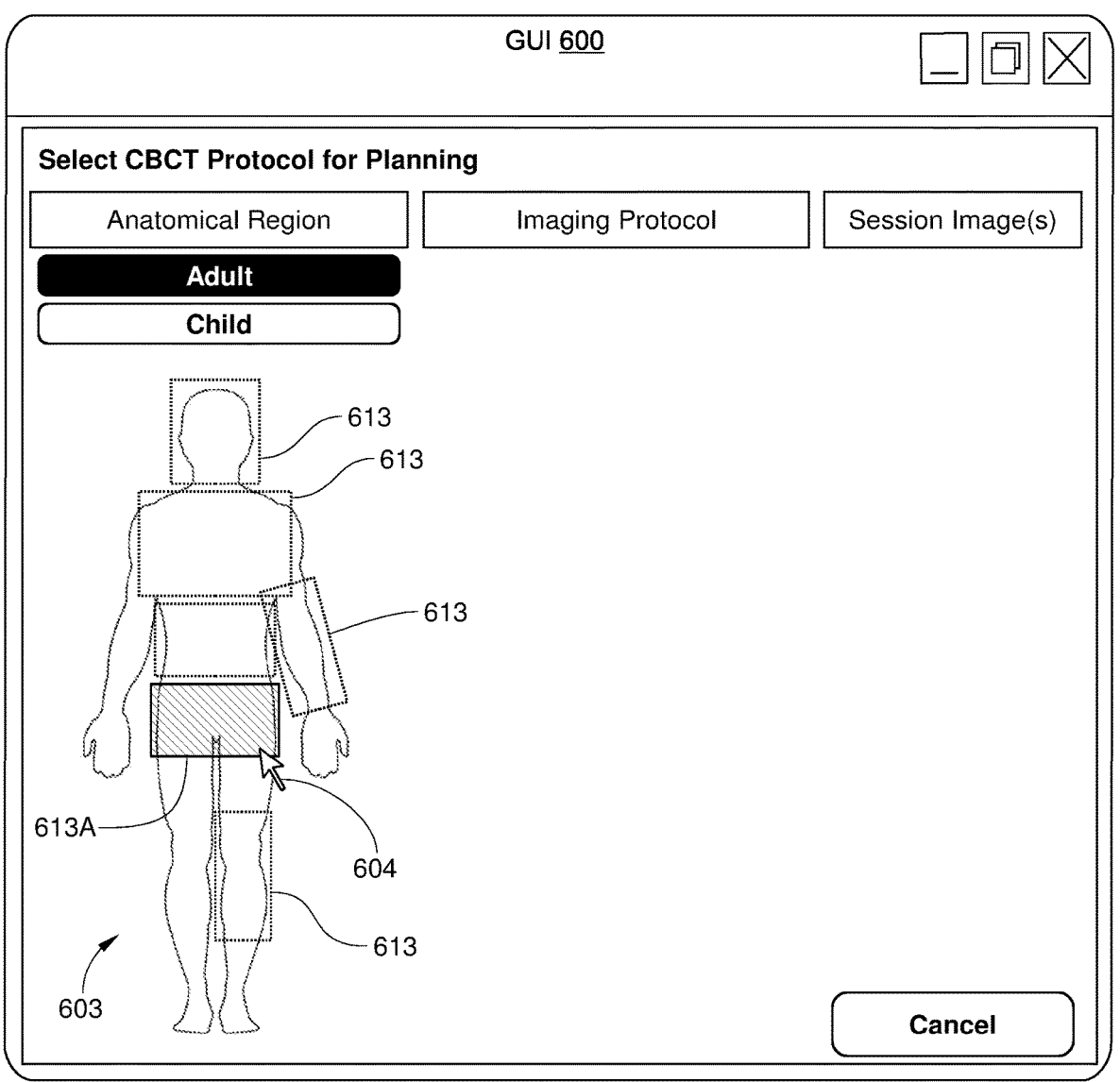

In step 503, in response to the user input received in step 502, RT system 100 displays one or more input elements 613 representing various anatomical regions, as shown in FIG. 6C. For example, in some embodiments, each of the one or more input elements 613 is displayed in conjunction with a corresponding patient avatar 603. Alternatively or additionally, in some embodiments, a particular input element 613A is highlighted or otherwise displayed with higher visual prominence when selected by the user and/or when hovered over by the user, for example with a cursor 604.

In step 504, RT system 100 receives a user input indicating a selected anatomical region. In some embodiments, the user input can be received when the user makes an appropriate selection with GUI 600, for example via an input element 613 of GIU 600.

Figure 6D:
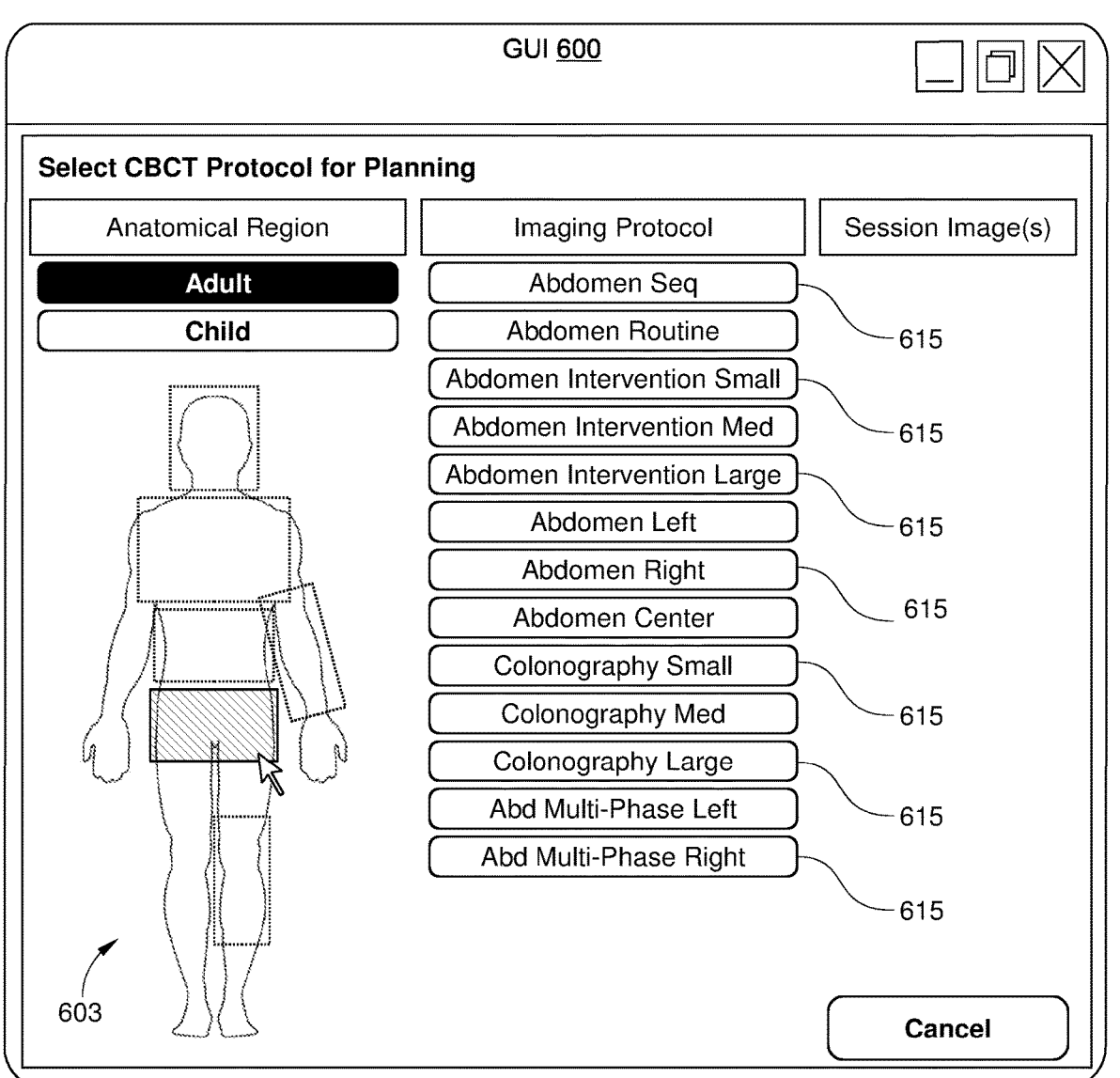

In step 505, in response to the user input received in step 504, RT system 100 displays one or more input elements 615 representing various imaging protocols, as shown in FIG. 6D. In some embodiments, each input element 615 corresponds to a different imaging protocol that is associated with the anatomical region selected in step 504. In the embodiment illustrated in FIG. 6D, a large number of different imaging protocols are associated with the anatomical region selected in step 504. Therefore, to facilitate user selection of an appropriate imaging protocol, in some embodiments, selection of a particular imaging protocol (as described below in step 506) displays the one or more session images that are to be acquired for that particular imaging protocol. In such embodiments, each session image corresponds to a different imaging mode. As noted previously, each imaging mode includes a specific combination of imaging parameter values for RT system 100.

Figure 6E:
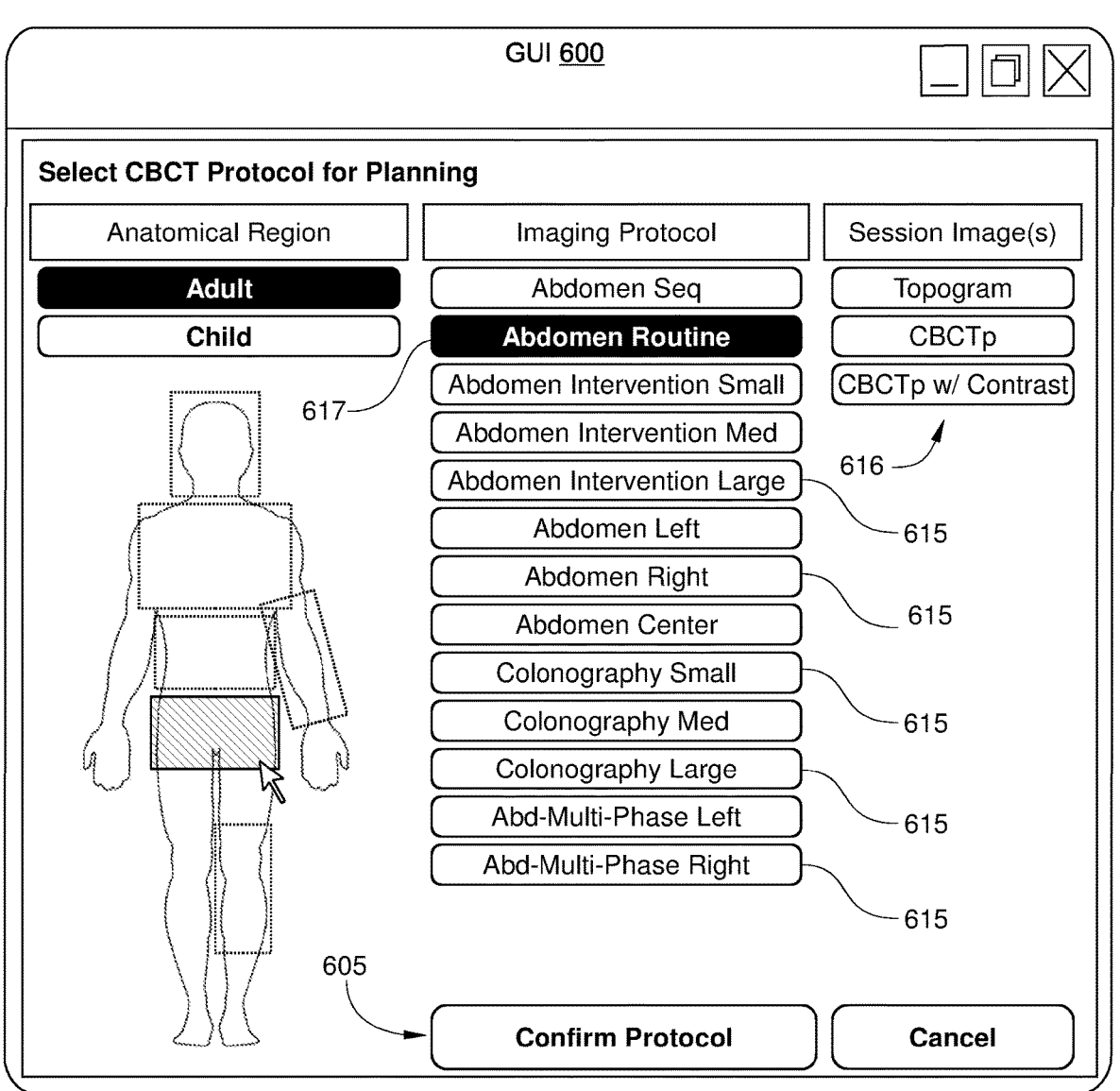

In step 506, RT system 100 receives a user input indicating a selected imaging protocol 617 for viewing, as shown in FIG. 6E. In some embodiments, the user input can be received when the user makes an appropriate selection with GUI 600, for example via an input element 615 of GIU 600.

In step 507, in response to the user input received in step 506, RT system 100 displays one or more input elements 616 representing the various session images associated with selected imaging protocol 617 selected in step 506. In some embodiments, RT system 100 further displays a confirm protocol button 605 when selected imaging protocol 617 is selected.

Each input element 616 corresponds to a different session image that is included in the imaging protocol selected in step 506. In the embodiment illustrated in FIG. 6E, three session images are included in selected imaging protocol 617: a topogram, a CBCT for planning, and a CBCT for planning with contrast. Thus, for the user to complete selected imaging protocol 617, the session images topogram, CBCT for planning, and CBCT for planning with contrast are all acquired. It is noted that each of the three session images included in selected imaging protocol 617 is associated with a different imaging mode that includes a specific combination of imaging parameter values for RT system 100. In some embodiments, to facilitate user selection of an appropriate imaging protocol from a large number of available imaging protocols, GUI 600 enables a user to preview the imaging parameter values associated with each such imaging mode. One such embodiment is described below in conjunction with steps 521 and 522 of method 500.

In step 508, RT system 100 receives a user input indicating selected imaging protocol 617 has been selected by the user to be loaded and performed. In some embodiments, the user input can be received when the user makes an appropriate selection with GUI 600, for example via confirm protocol button 605 of GIU 600.

Figure 6F:
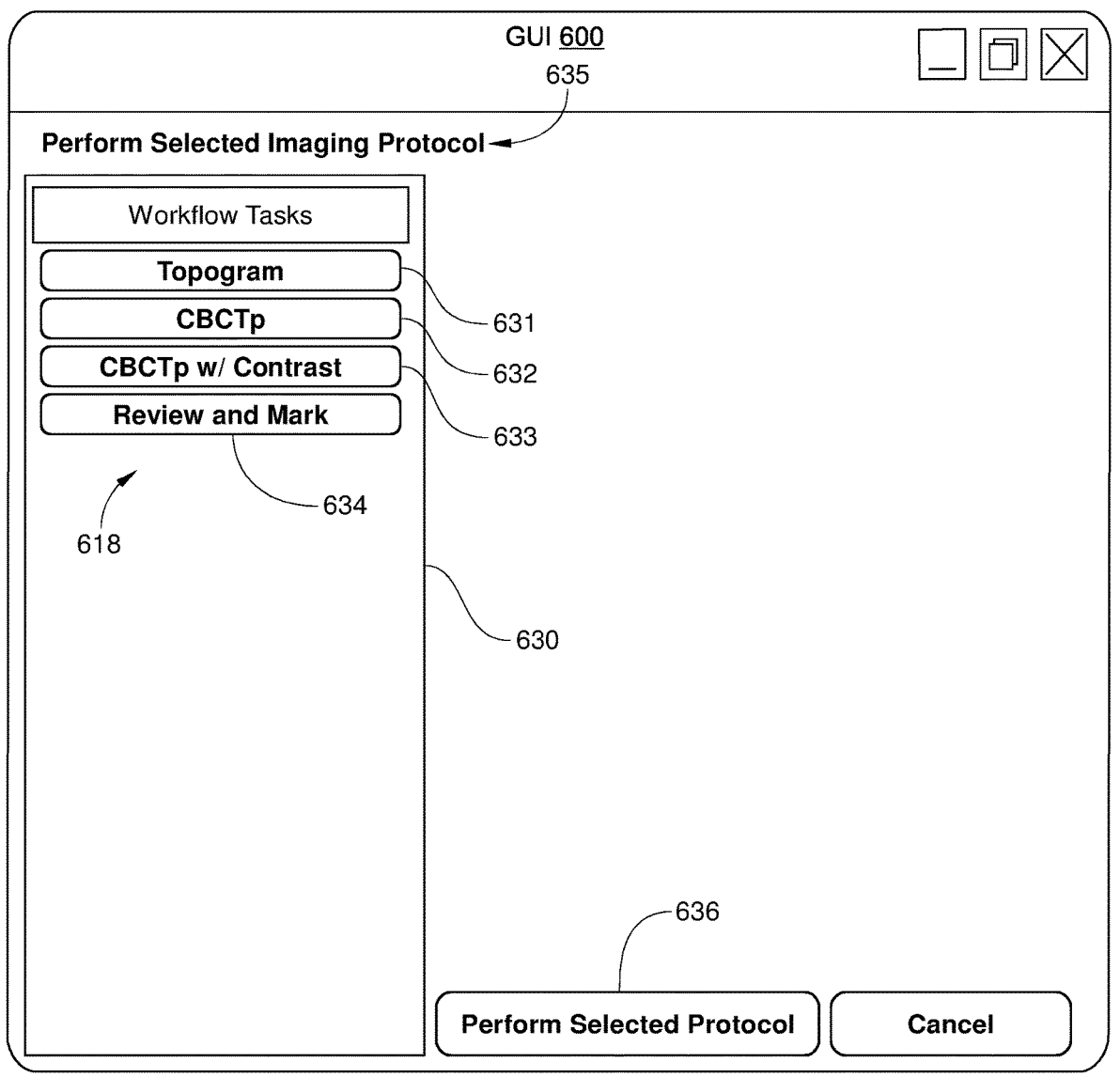

In step 509, in response to the user input received in step 508, RT system 100 displays workflow task indicators 618 for selected imaging protocol 617 in a workspace 630 of GUI 600, as shown in FIG. 6F. Each workflow task indicator 618 depicts a different workflow task that is associated with the selected imaging protocol 617 illustrated in FIG. 6E. Thus, GUI 600 can guide a user through the sequence of workflow tasks that are included in selected imaging protocol 617 to complete selected imaging protocol 617. In the embodiment illustrated in FIG. 6F, four workflow tasks are included in selected imaging protocol 617: a Topogram task 631, a CBCT for Planning task 632, a CBCT for Planning with Contrast task 633, and a Review and Mark task 634. Thus, for the user to complete selected imaging protocol 617, a topogram of the patient is acquired in Topogram task 631, a CBCT image is acquired in CBCT for Planning task 632, a contrast medium is administered and then a CBCT is acquired in CBCT for Planning with Contrast task 633, and a planning target volume is located and marked in Review and Mark task 634. In the embodiment illustrated in FIG. 6F, GUI 600 further includes a user prompt 635 indicating textually that the user must "Perform Selected Imaging Protocol." GUI 600 further includes a "Perform Selected Task" button 636 for initiation a selected workflow task in workspace 630. Alternatively, in some embodiments, once an imaging protocol has been selected with a user input via GUI 600, RT system 100 loads the imaging protocol (for example to treatment control computer 106 and/or remote control console 110) and a user can proceed with the workflow of that imaging protocol. In such embodiments, the workflow tasks of the loaded imaging protocol may be automatically selected as a user proceeds through the loaded imaging protocol, and each workflow task is not initiated based on a user input. In such embodiments, step 510 is not performed.

In some embodiments, workspace 630 is configured to mirror or otherwise appear visually similar to a treatment workflow workspace that is displayed when the user performs the steps of a radiation therapy treatment workflow using RT system 100. Thus, in such embodiments, the user performs the workflow steps of a radiation treatment protocol or a treatment planning imaging protocol while being prompted with similar UI elements. As a result, a user trained for performing radiation treatment protocols with RT system 100 can generally perform treatment planning scans with RT system 100 based on little additional training. It is noted that in safety-sensitive industries, such as health care, maintaining the same mental model for user can significantly reduce the risk of user error, for example by using visually similar workflow workspaces for different processes.

In step 510, RT system 100 receives a user input indicating that a particular workflow task has been selected by the user to be performed. In some embodiments, the user input can be received when the user makes a selection with GUI 600, for example via a particular workflow task indicator 618 of GIU 600. Alternatively or additionally, in some embodiments, the user input can be received when the user makes a selection via a UI element of GUI 600 that is associated with a particular workflow task indicator 618, such as a radio button, checkbox, and/or the like. As noted above, in some embodiments, RT system 100 guides a user through the workflow tasks of a particular imaging protocol. In such embodiments, step 510 is not performed.

In step 511, in response to the user input received in step 510, RT system 100 displays one or more prompts associated with the selected workflow task. For example, such prompts can include textual and/or graphical guidance for positioning a patient on couch 107 and/or loading the patient to a specified imaging location, reminding the user to administer a prescribed contrast medium, requesting boundaries for a topogram scan of the patient, reminding the user to properly immobilize the patient, providing appropriate breath-hold guidance to the patient during the selected workflow task, marking a planning target volume of the patient, and the like. Generally, the prompts provided in step 511 depend on the currently selected workflow task. In some embodiments, RT system 100 prevents subsequent steps of the selected workflow task from being completed until actions and/or user inputs indicated in such prompts are completed by the user. In some embodiments, RT system 100 displays such prompts at treatment control computer 106 or remote control console 110, depending on the specific workflow task.

In step 512, in response to the necessary user inputs being received in step 511, RT system 100 performs the selected workflow task, such as acquiring a topogram of the patient or acquiring a CBCT treatment planning image of the patient.

In step 513, RT system 100 determines whether there are any remaining workflow tasks associated with the selected imaging protocol. If yes, method returns to step 510; if no, method 500 proceeds to step 530 and terminates.

Figure 6G:
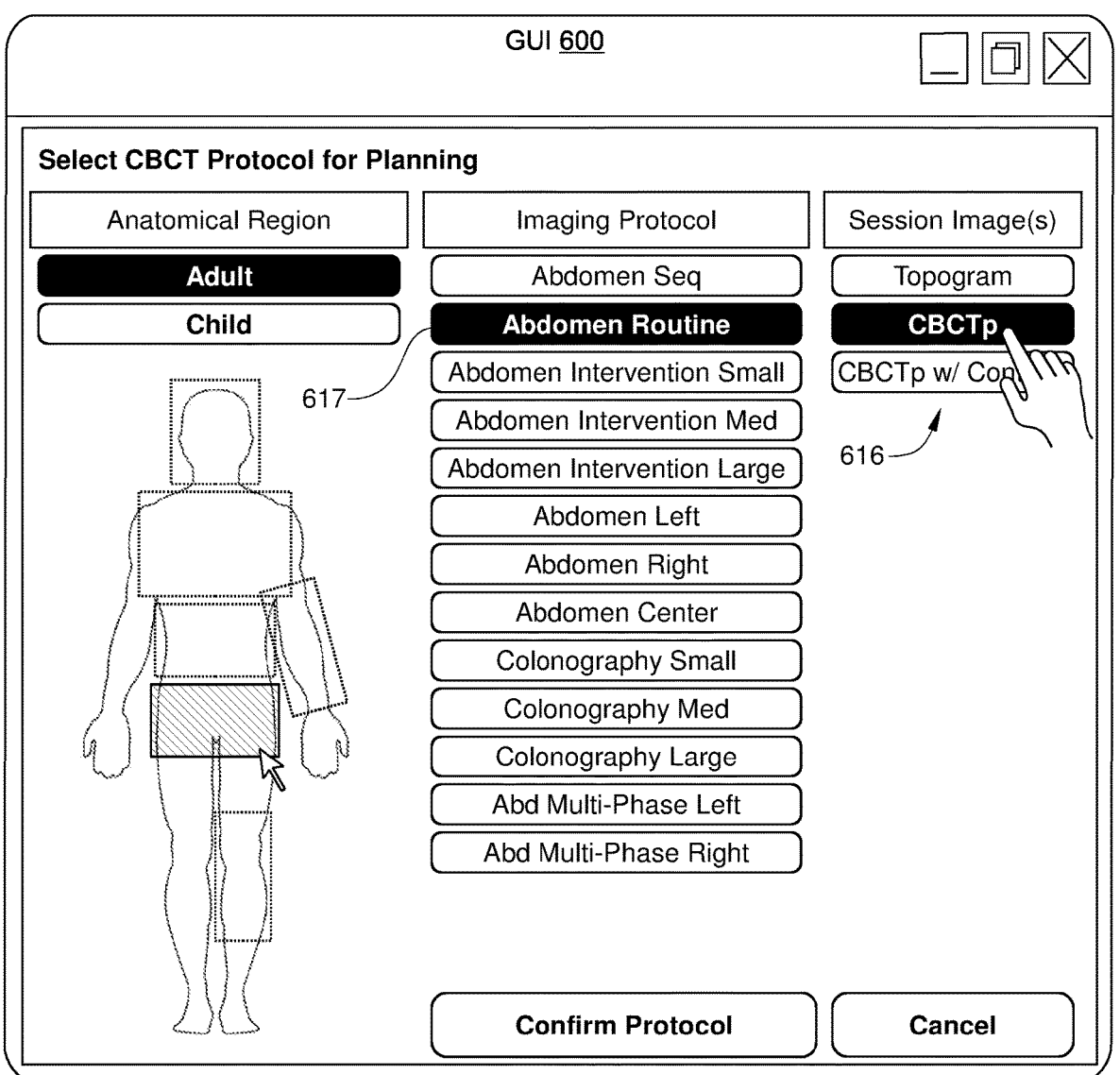

Steps 521 and 522 can be performed when input elements 616 representing the various session images associated with selected imaging protocol 617 are displayed, as described in step 507. In step 521, RT system 100 receives a user input indicating a particular session image of the imaging protocol is selected for viewing but not loading in step 507. In some embodiments, the user input can be received when the user makes an appropriate selection with GUI 600, as shown in FIG. 6G. For example, in some embodiments, the appropriate selection is made by the user via an input element 616 that corresponds to the particular imaging mode, for example when a user wants to view information associated with the particular imaging mode.

Figure 6H:
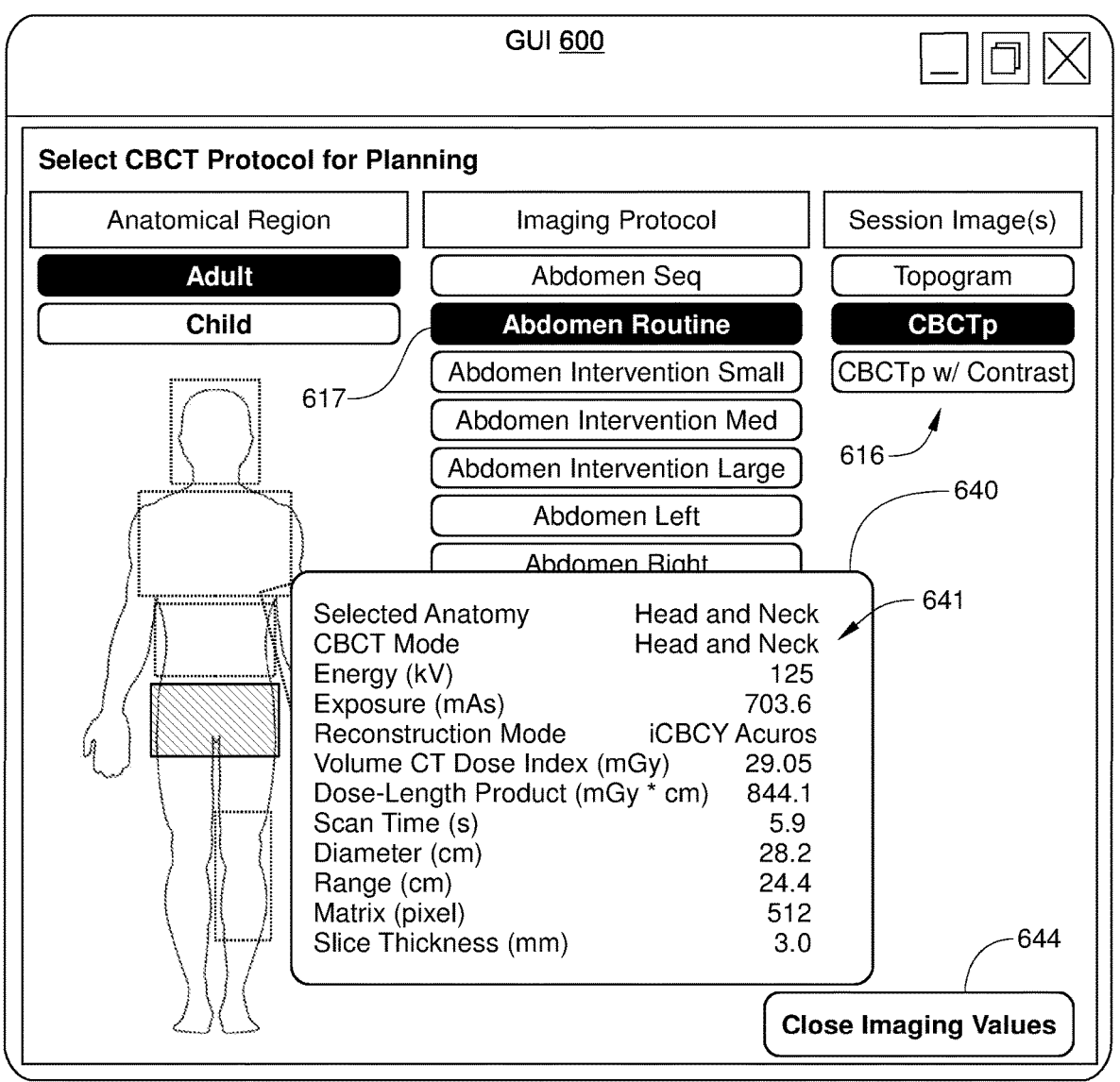

In step 522, RT system 100 displays values for imaging parameters 641 of the particular imaging mode selected in step 521, as shown in FIG. 6H. In some embodiments, the values for imaging parameters 641 are displayed in a workspace 640 or other display region of GUI 600. Display of the values for imaging parameters 641 in workspace 640 enables a user to confirm that the particular imaging mode selected in step 521 is suitable for the current patient, and thus whether the selected imaging protocol should be confirmed and implemented. In the embodiment illustrated in FIG. 6H, imaging parameters 641 include Selected Anatomy, CBCT Mode, Energy (kV), Exposure (mAs), Reconstruction Mode, Volume CT Dose Index (mGy), Dose-Length Product (mGy*cm), Scan Time (s), Diameter (cm), Range (cm), Matrix (pixel), and Slice Thickness (mm). In some embodiments, in step 522, some or all of imaging parameters 641 displayed in workspace 640 are "read only," and cannot be changed by a user. In some embodiments, workspace 640 further includes a Close Imaging Values button 644 for closing workspace 640.

Alternatively, in some embodiments, steps 521 and 522 are not available to a user. In such embodiments, a user can select an imaging protocol (for example in step 506) and review the session images that are included in the selected imaging protocol (for example in step 507), but cannot access workspace 640 or view specific imaging parameters 641.

Implementation of method 500 enables a user of RT system 100 to efficiently setup and perform a treatment planning scan. A structured workflow guides the user in a repeatable, easily followed process that ensures selection of the optimal imaging modes for a particular treatment planning scan session. In addition, the workflow steps of the treatment planning scan can include prompts with similar UI elements to radiation treatment protocols performed on the same RT system, so that a user familiar with performing radiation treatment protocols can use the same mental model when performing a treatment planning scan session. Further, in some embodiments, a UI of RT system 100 enables the user to review specific imaging modes and associated imaging parameter settings prior to being selected, which enables the user to confirm that the appropriate imaging mode is selected before being performed.

Exemplary Computing Device

Figure 7:
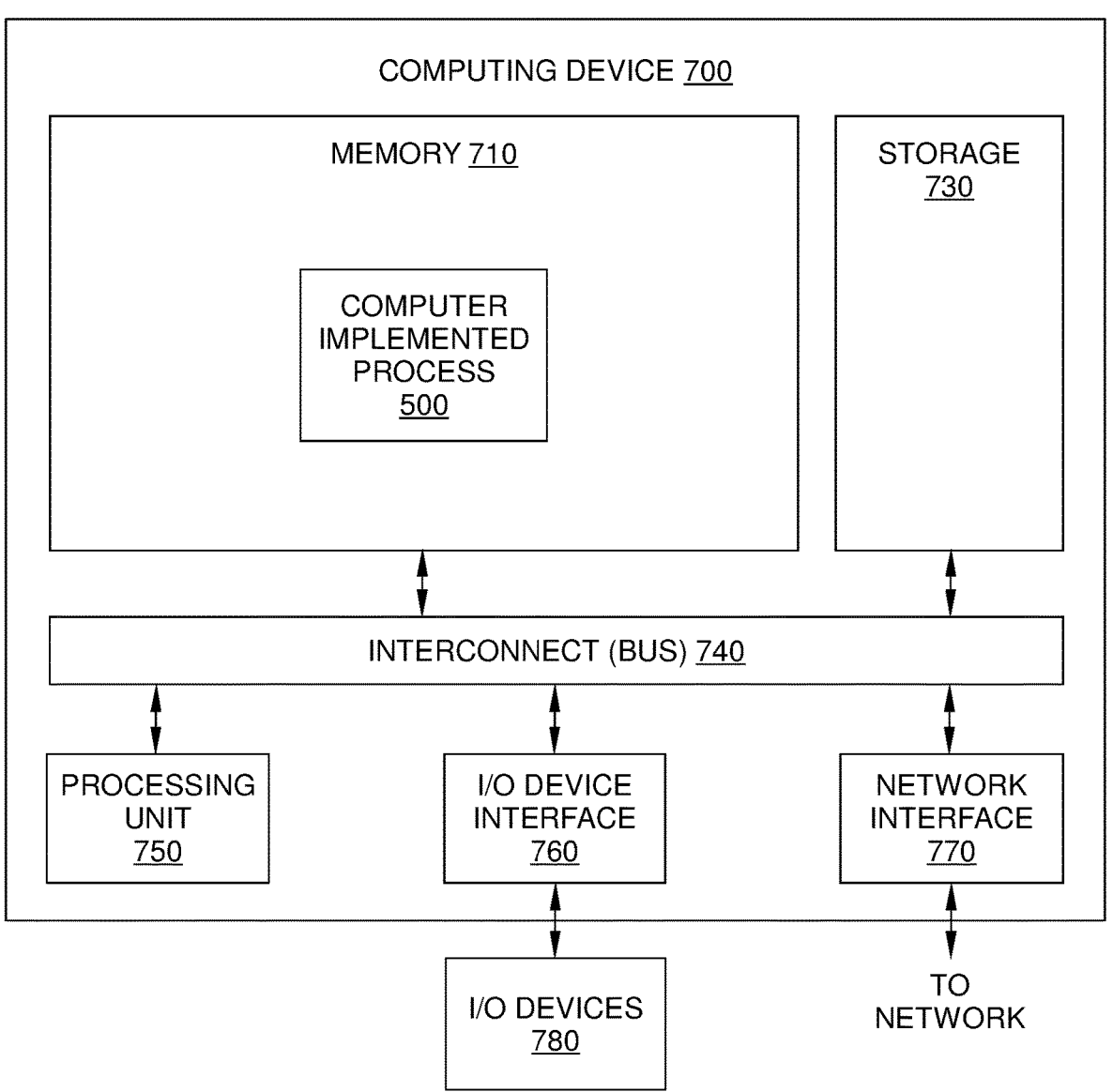
FIG. 7 is an illustration of a computing device configured to perform various embodiments of the present disclosure.

FIG. 7 is an illustration of computing device 700 configured to perform various embodiments of the present disclosure. Thus, in some embodiments, computing device 700 is implemented as or associated with image acquisition and treatment control computer 106 and/or remote control console 110. Computing device 700 may be a desktop computer, a laptop computer, a smart phone, or any other type of computing device suitable for practicing one or more embodiments of the present disclosure. In operation, computing device 700 is configured to execute instructions associated with computer-implemented method 500 as described herein. It is noted that the computing device described herein is illustrative and that any other technically feasible configurations fall within the scope of the present disclosure.

As shown, computing device 700 includes, without limitation, an interconnect (bus) 740 that connects a processing unit 750, an input/output (I/O) device interface 760 coupled to input/output (I/O) devices 780, memory 710, a storage 730, and a network interface 770. Processing unit 750 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 750 may be any technically feasible hardware unit capable of processing data and/or executing software applications, including computer-implemented method 500.

I/O devices 780 may include devices capable of providing input, such as a keyboard, a mouse, a touch-sensitive screen, and so forth, as well as devices capable of providing output, such as a display device and the like. Additionally, I/O devices 780 may include devices capable of both receiving input and providing output, such as a touchscreen, a universal serial bus (USB) port, and so forth. I/O devices 780 may be configured to receive various types of input from an end-user of computing device 700, and to also provide various types of output to the end-user of computing device 700, such as displayed digital images or digital videos. In some embodiments, one or more of I/O devices 780 are configured to couple computing device 700 to a network.

Memory 710 may include a random access memory (RAM) module, a flash memory unit, or any other type of memory unit or combination thereof. Processing unit 750, I/O device interface 760, and network interface 770 are configured to read data from and write data to memory 710. Memory 710 includes various software programs that can be executed by processor 750 and application data associated with said software programs, including computer-implemented method 500.

Figure 8:
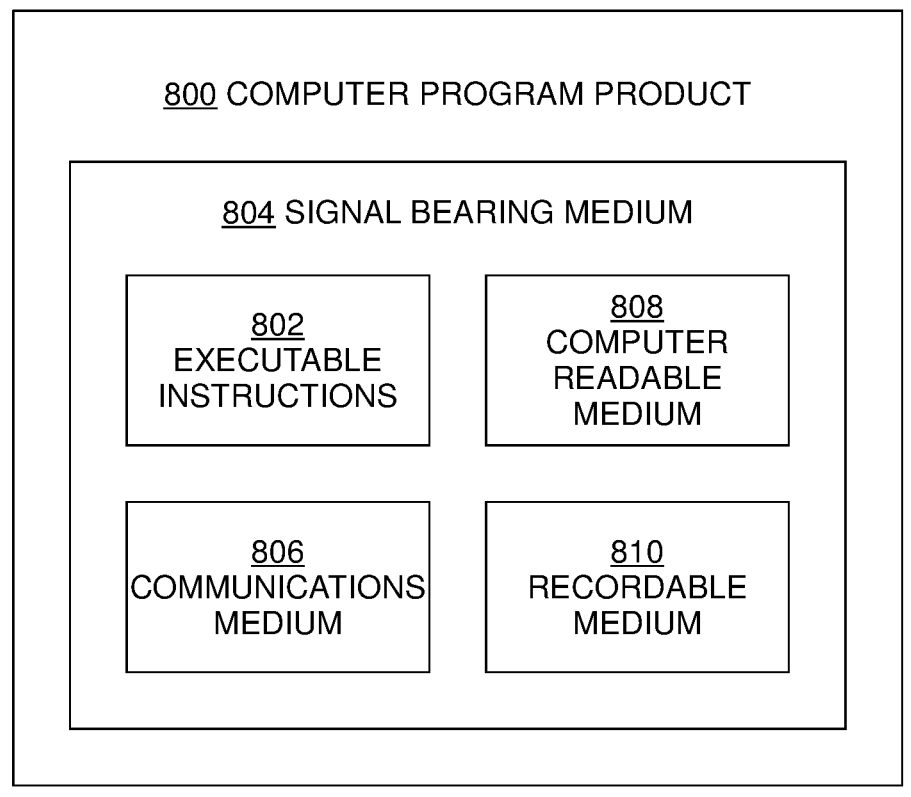
FIG. 8 is a block diagram of an illustrative embodiment of a computer program product for implementing one or more embodiments of the present disclosure.

FIG. 8 is a block diagram of an illustrative embodiment of a computer program product 800 for implementing a method for segmenting an image, according to one or more embodiments of the present disclosure. Computer program product 800 may include a signal bearing medium 804. Signal bearing medium 804 may include one or more sets of executable instructions 802 that, when executed by, for example, a processor of a computing device, may provide at least the functionality described above with respect to FIGS. 1-7.

In some implementations, signal bearing medium 804 may encompass a non-transitory computer readable medium 808, such as, but not limited to, a hard disk drive, a Compact Disc (CD), a Digital Video Disk (DVD), a digital tape, memory, etc. In some implementations, signal bearing medium 804 may encompass a recordable medium 810, such as, but not limited to, memory, read/write (R/W) CDs, R/W DVDs, etc. In some implementations, signal bearing medium 804 may encompass a communications medium 806, such as, but not limited to, a digital and/or an analog communication medium (e.g., a fiber optic cable, a waveguide, a wired communications link, a wireless communication link, etc.). Computer program product 800 may be recorded on non-transitory computer readable medium 808 or another similar recordable medium 810.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A radiation treatment system comprising:
   a treatment-delivering X-ray source configured to rotate about an isocenter of the radiation treatment system and direct treatment X-rays to a target volume;
   an imaging X-ray source configured to rotate about the isocenter of the radiation treatment system and direct imaging X-rays to a target region that includes the target volume; and
   a processor configured to perform:
      displaying a first set of multiple first user input elements within a graphical user interface of the radiation treatment system, wherein each first user input element corresponds to a different anatomical region;

in response to receiving a first user input via a specific first user input element included in the first set, displaying a second set of multiple second user input elements within the graphical user interface, wherein each second user input element corresponds to a different imaging protocol for an anatomical region that is associated with the specific first user input element in the first set;

in response to receiving a second user input via a specific second user input element included in the second set, selecting an imaging protocol that is associated with the specific second user input element;

in response to receiving a third user input confirming the selected imaging protocol, displaying, in a workspace within the graphical user interface, a plurality of workflow task indicators depicting respective workflow tasks that are associated with the selected imaging protocol, wherein the workflow task indicators are arranged in a sequence for executing the workflow tasks to complete the selected imaging protocol; and performing at least one of the workflow tasks to acquire at least one X-ray image of the target region via the imaging X-ray source.

2. The radiation treatment system of claim 1, further comprising a gantry on which the treatment-delivering X-ray source and the imaging X-ray source are mounted.

3. The radiation treatment system of claim 2, wherein the gantry is rotatably coupled to a drive stand of the radiation therapy system.

4. The radiation treatment system of claim 2, wherein the gantry rotates about a bore of the radiation treatment system.

5. The radiation treatment system of claim 1, wherein the isocenter is disposed in a bore of the radiation treatment system.

6. The radiation treatment system of claim 1, wherein the performing at least one of the workflow tasks comprises performing a cone-beam computed tomography (CBCT) imaging process with the imaging X-ray source via one or more imaging parameter values that are included in the imaging protocol.

7. The radiation treatment system of claim 1, wherein the at least one X-ray image of the target region comprises a set of multiple X-ray images, and the processor is further configured to perform generating a three-dimensional digital volume of the target region based on the set of multiple X-ray images.

8. The radiation treatment system of claim 1, further comprising:

receiving a treatment protocol that is based on the at least one X-ray image of the target region; and directing the treatment X-rays to the target volume based on the treatment protocol.

9. The radiation treatment system of claim 1, wherein the selected imaging protocol includes at least one of a reconstruction mode that indicates a specific reconstruction algorithm that is employed for generating a three-dimensional digital volume of the target region, at least one imaging mode that includes a set of imaging parameter values for operation of the imaging X-ray source while acquiring the at least one X-ray image of the target region, or a contrast administration mode that includes one or more parameter values associated with contrast administration.

10. The radiation treatment system of claim 9, wherein the set of imaging parameter values are associated with the anatomical region.

11. The radiation treatment system of claim 9, wherein the at least one imaging mode includes one or more of a topogram imaging mode for the anatomical region, a CBCT-for-treatment-planning mode for the anatomical region, or a CBCT-for-treatment-planning mode with contrast medium for the anatomical region.

12. The radiation treatment system of claim 1, further comprising, in response to receiving a fourth user input via a specific third user input element included in a third set of multiple third user input elements within the graphical user interface for a specific imaging mode associated with the selected imaging protocol, displaying at least one parameter value associated with the specific imaging mode within the graphical user interface, wherein each third user input element corresponds to a different imaging mode associated with the selected imaging protocol.

13. The radiation treatment system of claim 1, wherein the selected imaging protocol includes information associated with the imaging of a particular patient.

14. The radiation treatment system of claim 13, wherein the information associated with the imaging of the particular patient includes at least one of a patient size, an anatomical region, contrast information for the particular patient, breath hold information for the particular patient, slice thickness, and specialized imaging dose for the particular patient.

15. The radiation treatment system of claim 1, wherein the processor is further configured to perform displaying imaging parameter values associated with one of the workflow tasks being selected for further confirmation that the workflow task is suitable for a particular patient.

16. A computer-implemented method for a radiation treatment system that includes a processor, a treatment-delivering X-ray source configured to rotate about an isocenter of the radiation treatment system and direct treatment X-rays to a target volume and an imaging X-ray source configured to rotate about the isocenter of the radiation treatment system and direct imaging X-rays to a target region that includes the target volume, the method comprising:

displaying, by the processor of the radiation treatment system, a first set of multiple first user input elements within a graphical user interface of the radiation treatment system, wherein each first user input element corresponds to a different anatomical region;

in response to receiving a first user input via a specific first user input element included in the first set, displaying, by the processor, a second set of multiple second user input elements within the graphical user interface, wherein each second user input element corresponds to a different imaging protocol for an anatomical region that is associated with the specific first user input element in the first set;

in response to receiving a second user input via a specific second user input element included in the second set, selecting, by the processor, an imaging protocol that is associated with the specific second user input element;

in response to receiving a third user input confirming the selected imaging protocol, displaying, by the processor, in a workspace within the graphical user interface, a plurality of workflow task indicators depicting respective workflow tasks that are associated with the selected imaging protocol, wherein the workflow task indicators are arranged in a sequence for executing the workflow tasks to complete the selected imaging protocol; and performing, by the processor, at least one of the workflow tasks to acquire at least one X-ray image of the target region by rotating the imaging X-ray source about the isocenter based on the selected imaging protocol that is associated with the specific second user input element.

17. The computer-implemented method of claim 16, further comprising:

receiving a treatment protocol that is based on the at least one X-ray image of the target region; and directing the treatment X-rays from the treatment-delivering X-ray source to the target volume based on the treatment protocol.

18. The computer-implemented method of claim 16, wherein the selected imaging protocol includes at least one of a reconstruction mode that indicates a specific reconstruction algorithm that is employed for generating a three-dimensional digital volume of the target region, at least one imaging mode that includes a set of imaging parameter values for operation of the imaging X-ray source while acquiring the at least one X-ray image of the target region, or a contrast administration mode that includes one or more parameter values associated with contrast administration.

19. The computer-implemented method of claim 18, wherein the set of imaging parameter values are associated with the anatomical region.

20. The computer-implemented method of claim 18, wherein the at least one imaging mode includes one or more of a topogram imaging mode for the anatomical region, a CBCT-for-treatment-planning mode for the anatomical region, or a CBCT-for-treatment-planning mode with contrast medium for the anatomical region.

\*　\*　\*　\*　\*